United States Patent
Venkatasubramanian et al.

(10) Patent No.: US 6,897,308 B1
(45) Date of Patent: May 24, 2005

(54) PROCESS FOR THE PREPARATION OF ANTI-PSYCHOTIC 3-[2-[-4-(6-FLUORO-1,2-BENZIOSOXAZOL-3-YL)-1-PIPERIDINYL]ETHYL]-6,7,8,9-TETRAHYDRO-2-METHYL-4H-PYRIDO[1,2-A]PYRIMIDIN-4-ONE

(75) Inventors: Radhakrishnan Tarur Venkatasubramanian, Maharashtra (IN); Sathe Dhananjay Govind, Maharashtra (IN); Suryavanshi Chandrakant Vasantrao, Maharashtra (IN)

(73) Assignee: RGP Life Sciences Limited, Mumbai (IN)

( * ) Notice: Subject to any disclaimer, the term of this patent is extended or adjusted under 35 U.S.C. 154(b) by 0 days.

(21) Appl. No.: 10/257,981
(22) PCT Filed: May 5, 2000
(86) PCT No.: PCT/IN00/00053
§ 371 (c)(1),
(2), (4) Date: Oct. 29, 2002
(87) PCT Pub. No.: WO01/85731
PCT Pub. Date: Nov. 15, 2001

(51) Int. Cl.$^7$ ................. C07D 471/04; C07D 498/04
(52) U.S. Cl. .................................................. 544/282
(58) Field of Search ........................ 544/282

(56) References Cited

U.S. PATENT DOCUMENTS

| | | | |
|---|---|---|---|
| 4,355,037 A | 10/1982 | Strupczewki et al. | 424/267 |
| 4,804,663 A | 2/1989 | Kennis et al. | 514/258 |
| 4,957,916 A | 9/1990 | Kennis et al. | 514/254 |
| 5,015,740 A | 5/1991 | Kennis et al. | 544/366 |

FOREIGN PATENT DOCUMENTS

| | | |
|---|---|---|
| EP | 0196132 | 10/1986 |
| ES | 2050069 | 5/1994 |
| ES | 2074966 | 9/1995 |

OTHER PUBLICATIONS

English Language Abstract for Spainish Appln. No. 2074966, 1995.
"Synthesis of Drugs & Drug Intermediates" submitted to "The University of Mumbai" by Ms. Evelyn D. Lobo, Jun. 1996.

Primary Examiner—Richard L. Raymond
(74) Attorney, Agent, or Firm—Greenblum & Bernstein, P.L.C.

(57) ABSTRACT

A process for the preparation of 3-substituted ethyl-6,7,8,9-tetrahydro-2-methyl-4H-pyrido[1,2,-a]pyrimidin-4-one of the formula IIB:

Formula IIB

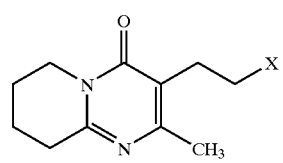

where X may be halo, acyloxy, or sulfonyloxy such as tosyloxy or mesyloxy, an intermediate in the synthesis of the anti-psychotic risperidone. The process comprises hydrogenation of 3-substituted ethyl-2-methyl-4H-pyrido[1,2-a]pyrimidin-4-one in aqueous inorganic acid medium at atmospheric to 60 psi at 0–100° C. in the presence of a metal catalyst and the product is isolated. A process for the preparation of risperidone of the formula I:

Formula I

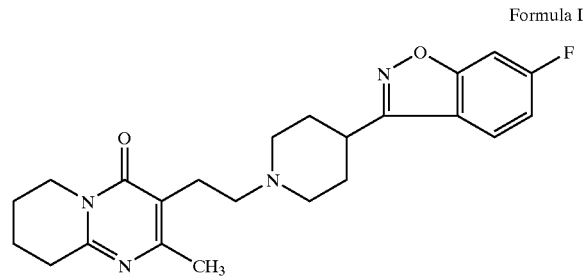

comprising condensation of 3-substituted ethyl-6,7,8,9-tetrahydro-2-methyl-4H-pyrido[1,2,-a]pyrimidin-4-one with 6-fluoro-3-(4-piperidinyl)-1,2-benzisoxazole in water in the presence of an inorganic base at 25–100° C. and the product is isolated.

20 Claims, No Drawings

PROCESS FOR THE PREPARATION OF ANTI-PSYCHOTIC 3-[2-[-4-(6-FLUORO-1,2-BENZIOSOXAZOL-3-YL)-1-PIPERIDINYL]ETHYL]-6,7,8,9-TETRAHYDRO-2-METHYL-4H-PYRIDO[1,2-A]PYRIMIDIN-4-ONE

This application is a 371 of PCT/IN00/00053, filed May 5, 2000.

TECHNICAL FIELD

The above compound is commonly known as risperidone and is of the formula I:

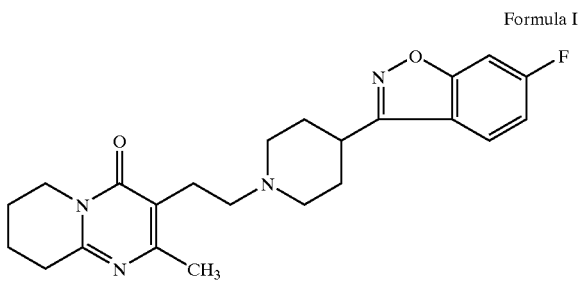

Formula I

Risperidone elicits its action by antagonising serotonine. Risperidone is a highly potent drug used in the treatment of schizophrenic states and also shows broader applications in other areas of psychosis.

BACKGROUND ART

Risperidone of the formula I is known to be prepared by the condensation of 3-(2-chloroethyl)-6,7,8,9-tetrahydro-2-methyl-4H-pyrido[1,2,-a]pyrimidin-4-one of the formula IIA:

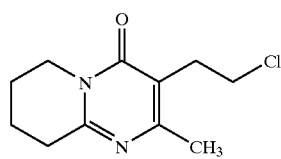

Formula IIA with 4-(2,4-difluorobenzoyl) piperidine of the formula III:

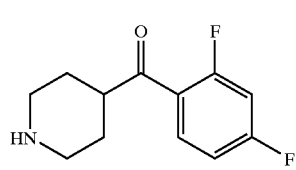

Formula III in organic solvent such as methylene dichloride, acetonitrile, N,N-dimethyl formamide (DMF) or N-methyl pyrrolidone in the presence of an inorganic base such as sodium hydroxide, carbonate or bicarbonate at 50–100° C., followed by oximation and cyclisation (Spanish Patent No 2,050, 069).

Inorganic bases used in the above reaction being sparingly to soluble in organic solvent used as medium for the reaction, they may not neutralise the acid by-product fast with the result that the neutralisation may be sluggish. Due to the slow removal of the acid by-product from the reaction mixture there are chances of decomposition of the condensation product thereby reducing the yield and purity thereof. The yield of condensation product obtained by this condensation process is low of the order of 63.1%. This process is therefore inefficient and uneconomical. The medium for the condensation being organic, isolation of the condensation product is to be carried out by quenching the reaction mixture with water followed by extraction with organic solvent such as methylene dichloride. Solvent extraction is cumbersome, lengthy and time-consuming and also engenders poor recovery of organic solvent used for the reaction. Also organic solvents such as DMF are reported to decompose in the presence of inorganic bases at elevated temperatures (Encyclopedia of Chemical,Technology, 3rd edition, 11, 263) further complicating isolation. Besides, use of organic solvents as medium for the reaction makes die process further expensive and uneconomical. Moreover, solvents such as DMF are hazardous and pollute environment when used in large scale and also entail effluent disposal/treatment problems.

Risperidone of Me formula I may also be prepared by the condensation of chlorotetrahydro pyridopyrimidine of the formula IIA with 6-fluoro-3-(4-piperidinyl)-1,2-benzisoxazole of the formula IV:

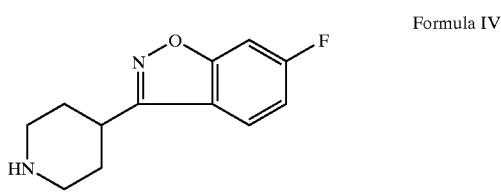

Formula IV in an organic solvent such as DMF, 4-methyl-2-pentanone, benzene, ethanol, 1,4-dioxane, tetrahydrofuran, nitrobenzene or 1-methyl-2-pyrrolidinone in the presence of an organic base such as N,N-diethylethanamine, 4-ethyl morpholine or N-(1-methylethyl)-2-propanamine or an inorganic base such as sodium or potassium carbonate, sodium hydrogen carbonate or sodium methoxide, hydroxide or hydride, usually at 85–90° C. (U.S. Pat. No. 4,804,663). The organic bases which may be used in the above condensation are expensive and their use makes the above reaction uneconomical. Inorganic bases when used in organic solvent medium may result in decomposed condensation product as earlier discussed. The yield of the product obtained by this method is low of the order of 46% and renders the process inefficient and uneconomical. The reaction medium being organic, the isolation of the condensation product is to be carried out by quenching the reaction mixture with water followed by filtration of the resulting solid and recrystallsation thereof from an organic solvent such as DMF. This isolation procedure besides being cumbersome, suffers from poor solvent recovery. Also due to use of inorganic bases in organic solvent such as DMF, isolation becomes further complicated for reasons as explained earlier. Organic solvents used as reaction medium further makes the process expensive and uneconomical. Also this process is not free from the disadvantages due to use of solvents such as DMF as aforesaid.

The intermediate chloro tetrahydro pyridopyrimidine of the formula IIA in the synthesis of anti-psychotic risperidone of the formula I may be obtained by hydrogenation of 3-(2-chloroethyl)-2-methyl-4H-pyrido[1,2,-a]pyrimidin-4-one of the formula VA:

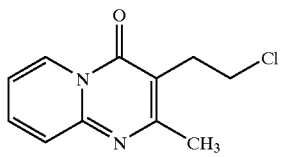

Formula VA in acetic acid medium at 50 psi and at 25–30° C. in the presence of Pd/C catalyst. (A Thesis entitled "Synthesis of Drugs & Drug Intermediates" submitted to "The University Of Mumbai" by Ms Evelyn D Lobo, p35, June 1996, for the degree of M Pharm Sci.). This hydrogenation may produce predominantly dechlorinated compounds as by-products, since dechlorination may be accelerated in acetic acid medium. This may result in low yield and purity of the product. The yield of the product obtained by this method is low of the order of 77%, thus making this process inefficient and uneconomical. The isolation of the product involves filtration of the catalyst followed by evaporation of acetic acid from the reaction mixture, dissolving the resulting residue in a solvent, deacidification and evaporation of solvent followed by recrystallisation of the resulting solid from 2-propanol. Such mutiple steps for isolation are cumbersome, lengthy and time consuming. Acetic acid is a hazardous and flammable solvent and pollutes the environment when used in large scale. Also its use makes the process expensive and further uneconomical.

The chloro tetrahydro pyridopyrimidine reactant of the formula IIA may also be prepared by hydrogenation of the 3-(2-hydroxyethyl)-2-methyl-4H-pyrido[1,2,-a]pyrimidin-4-one of the formula VI:

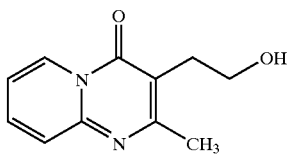

Formula VI using Pd/C catalyst in aqueous ethanol at 25–30° C. followed by reacting the resulting hydroxyethyl tetrahydro pyridopyrimidine compound of the formula VII:

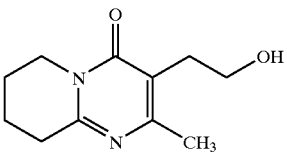

Formula VII with thionyl chloride in methylene chloride at 25–30° C. for 24 hours (Spanish Patent No 2,050,069). This route involves two steps for the preparation of the compound of the formula IIA and is lengthy and time-consuming. Moreover, thionyl chloride is hazardous and when used in large scale, pollutes the environment. The overall yield of the product obtained by this method is low of the order of 44% due to two moderately yielding steps, thus making the process inefficient and uneconomical.

An object of the invention is to provide a process for the preparation of risperidone of the formula I, which is simple and less time consuming.

Another object of the invention is to provide a process for the preparation of risperidone of the formula I, which is inexpensive and economical.

Another object of the invention is to provide a process for the preparation of risperidone of the formula I, which results in high yield and purity of risperidone and is efficient.

Another object of the invention is to provide a process for the preparation of risperidone of the formula I, which is safe and does not pollute the environment.

Another object of the invention is to provide a process for the preparation of risperidone of the formula I, which is commercially feasible.

Another object of the invention is to provide a process for the preparation of tetrahydro pyridopyrimidine of the formula IIB, which is simple and less time consuming.

Another object of the invention is to provide a process for the preparation of tetrahydro pyridopyrimidine of the formula IIB, which is inexpensive and economical.

Another object of the invention is to provide a process for the preparation of tetrahydro pyridopyrimidine of the formula IIB, which results in high yield and purity of tetrahydro pyridopyrimidine and is efficient.

Another object of the invention is to provide a process for the preparation of chlorotetrahydro pyridopyrimidine of the formula IIB, which is safe and does not pollute the environment.

Another object of the invention is to provide a process for the preparation of chlorotetrahydro pyridopyrimidine of the formula IIB, which is commercially feasible.

DISCLOSURE OF THE INVENTION

According to the invention there is provided a process for the preparation of substituted ethyl-6,7,8,9-tetrahydro-2-methyl-4H-pyrido[1,2,-a]pyrimidin-4-one of the formula IIB:

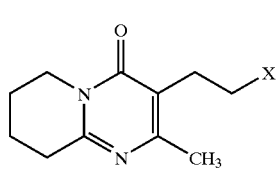

Formula IIB where X may be halo, acyloxy, or sulfonyloxy such as tosyloxy or mesyloxy, comprising hydrogenation of 3-substituted ethyl-2-methyl-4H-pyrido[1,2,-a]pyrimidin-4-one of the formula VB:

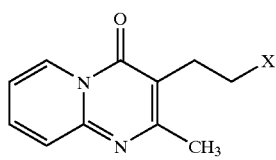

Formula VB in aqueous inorganic acid medium at atmospheric to 60 psi at 0–100° C. in the presence of a metal catalyst followed by isolation of the resulting product.

According to the invention there is also provided a process for the preparation of anti-psychotic 3-[2-[4-(6-fluoro-1,2-benzisoxazol-3-yl)-1-piperidinyl]ethyl]-6,7,8,9-tetrahydro-2-methyl-4H-pyrido[1,2,-a]pyrimidin-4-one, commonly known as risperidone of the formula I:

Formula I

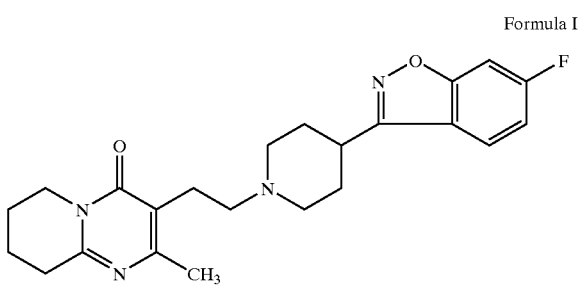

comprising condensation of 3-substituted ethyl-6,7,8,9-tetrahydro-2-methyl-4H-pyrido[1,2,-a]pyrimidin-one of the formula IIB:

Formula IIB

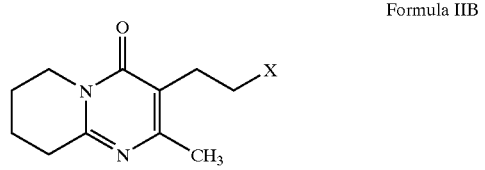

where X may be halo, acyloxy or sulfonyloxy such as tosyloxy or mesyloxy, with 6-fluoro-3-(4-piperidinyl)-1,2-benzisoxazole of the formula IV:

Formula IV

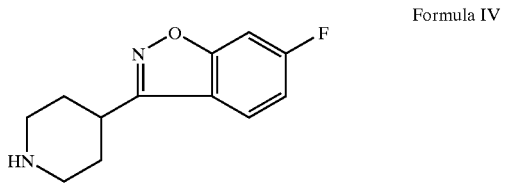

in water in the presence of an inorganic base at 25–100° C. followed by isolation of the resulting product.

The compound of the formula IIB is an intermediate in the synthesis of the anti-psychotic risperidone.

The term halo includes chloro, bromo or iodo. Preferably X may be chloro.

The pyridopyrimidine compound of the formula VB may be prepared in known manner. (A thesis entitled "Synthesis of Drugs and Drugs Intermediates" submitted to "The University of Mumbai" by Ms Evelyn D Lobo, p 30, June 1996, for due degree of M Pharm Sci.).

The inorganic acid in the aqueous medium for the hydrogenation may be sulfuric acid, hydrochloric acid or hydrobromic acid, preferably hydrochloric acid. The inorganic acid solubilises the pyridopyrimidine compound of the formula VB in aqueous medium by converting it to its water soluble salt, prior to hydrogenation.

The metal catalyst may be platinum, palladium, nickel, rhodium or ruthenium supported on solid support such as calcium carbonate, alumina, barium sulfate, silica or activated carbon. Preferably palladium supported on activated carbon may be used.

Preferably the reduction temperature may be 25–40° C.

Preferably the hydrogenation is carried out at pressure of 25 psi.

The isolation of the tetrahydro pyridopyrimidine of the formula IIB may be carried out by filtration of the metal catalyst followed by pH adjustment to 4–10 of the resulting mixture with a base such as an alkali metal hydroxide or carbonate. The resulting solid is then filtered at 0–50° C., preferably at 10–20° C. Alternatively the filtrate after removal of catalyst, may be directly subjected to insitu condensation with the compound of the is formula IV to produce risperidone.

The benzisoxazole compound of the formula IV may be prepared in known manner (U.S. Pat. Nos. 4,355,037 and 4,804,663).

The inorganic base used in the condensation may be an akali metal carbonate such as sodium, potassium or lithium carbonate or sodium bicarbonate or an alkaline earth metal carbonate such as calcium, barium or strontium carbonate or an alkali metal hydroxide such as sodium, potassium or lithium hydroxide or an alkaline earth metal hydroxide such as calcium, barium or strontium hydroxide. Preferably sodium carbonate may be used.

The condensation temperature may be preferably 60–90° C.

The isolation of risperidone from the reaction mixture is carried out by filtration at 25–400° C. followed by purification, preferably by crystallisation using organic solvents such as DMF or N,N-dimethyl acetamide or $C_{1-3}$ aliphatic alkanol or ether such as diethyl ether or diisopropyl ether or tetrahydrofuran or ketone such as 2-propanone, 2-butanone or 4-methyl-2-pentanone, preferably DMF.

The process of the invention for the preparation of the tetrahydro pyridopyrimidine of the formula IIB is carried out in aqueous medium because of which it proceeds at a controlled rate. Therefore dechlorination of the compound of the formula IIB when X is chloro, is prevented. The process of the invention results in high yield (83%) and purity (99%) of the product of the formula IIB and is efficient and economical. The tetrahydro pyridopyrimidine compound of the formula IIB is obtained from a single step reaction and eliminates multiple steps for isolation as described in the prior art. The procedure to isolate the product of the formula IIB obtained by the process of the invention comprises filtration of die catalyst pH adjustment and filtration of the resulting solid, and is therefore simple, less cumbersome, less tedious and less-time consuming when compared to the prior art methods. The compound of the formula IIB when subjected to insitu condensation makes the process for the preparation of risperidone further less time-consuming and economical. The process also eliminates hazardous solvents and pollution of the environment caused thereby and is safe to carry out. The use of water instead of organic solvents as medium for the reaction makes the process further inexpensive and economical and also eliminates solvent recovery/disposal/treatment problems as in the prior art. Due to the above reasons, this process is also commercially feasible.

According to the invention the process for the preparation of risperidone is carried out in an aqueous medium in the presence of an inorganic base. The solubility of the inorganic base in the aqueous medium being high, the neutralisation of the acid by-product formed during the condensation is fast by the inorganic base in solution form. This prevents degradation of risperidone by the acid by-product and also results in high yields (66–72%) and purity (~99%) thereof, thereby making the process efficient and economical. The process of the invention does not use organic bases and is inexpensive. The reaction medium being aqueous, quenching with water or extraction with organic solvents is unnecessary for isolation of risperidone. The isolation procedure involves a single step ie filtration and is therefore simple, less cumbersome and less time-consuming when compared to the prior art methods. The process eliminates use of hazardous solvents and pollution of the environment caused thereby and is safe. The use of water as medium instead of organic solvents is inexpensive and economical and eliminates solvent recovery/disposal/treatment problems as in the prior art. Due to the above reasons, the process of the invention is commercially feasible.

The following experimental examples are illustrative of the invention but not limitative of the scope thereof.

EXAMPLE 1

Preparation of 3-(2-chloroethyl)-6,7,8,9-tetrahydro-2-methyl-4H-pyrido[1,2,-a]pyrimidin-4-one of the Formula II A To a 500 ml hydrogenation flask was charged 3-(2-chloroethyl)-2-methyl-4H-pyrido[1,2,-a]pyrimidin-4-one (20.0 g, 99% pure by HPLC analysis), water (50.0 ml), 30% HCl (10.0 ml) and 10% Pd/C (2.0 g). The contents of the flask were reduced with hydrogen gas at pressure 25 psi under agitation for 6 hours at 30° C. The catalyst in the reaction mixture was filtered through Whatmann 1 filter paper. The filtrate free from catalyst was basified by addition of 45% caustic soda lye (6.0 ml). The product was filtered and dried.

The product obtained was characterised by Nuclear Magnetic Resonance (NMR) Spectrosopy as follows:

$^1$H NMR (60 MHz), CDCl$_3$: δ 3.7 (m, 4H); δ 2.9 (t, J=6 Hz, 2H); δ 2.3 (s, 3H); δ 1.8 (m, 6H).

Yield=16.6 g (83%).

Purity=99% [when analysed by High Performance Liquid Chromatography (HPLC)].

EXAMPLE 2

Preparation of 3-[2-[4-(6-fluoro-1,2-benzisoxazol-3-yl)-1-piperidinyl]ethyl]-6,7,8,9-tetrahydro-2-methyl-4H-pyrido[1,2,-a]pyrimidin-4-one (Risperidone of the Formula I)

To a 10 L flask was charged the tetrahydro pyridopyrimidine (666.0 g) of Example 1, water (3330.0 ml) and 6-fluoro-3-(4-piperidinyl)-1,2-benzisoxazol (639.0 g) and sodium carbonate (1152.0 g). The contents of the flask were heated to 85–90° C. and stirred for 4 hours. The reaction mixture was cooled to room temperature and filtered. The product was purified by crystallisation from DMF.

The product was characterised by NMR spectroscopic studies as follows: p$^1$H NMR (60 MHz, CDCl$_3$): δ 7.5–7.9 (m, 1H); δ 6.8–7.45 (m, 2H); δ 3.8–4 (m, 2H); δ 2.45–3.5 (m, 11H); δ 2.35 (s, 3H); δ 1.65–2.25 (m, 8H).

Yield=865.0 g (72%).

Purity=99% (when analysed by HPLC).

EXAMPLE 3

Preparation of 3-[2-[4-(6-fluoro-1,2-benzisoxazol-3-yl)-1-piperidinyl]ethyl]-6,7,8,9-tetrahydro-2-methyl-4H-pyrido[1,2,-a]pyrimidin-4-one (Risperidone of the Formula I) by One-pot Reaction The filtrate free from catalyst of Example 1 was neutralised by addition of 45% caustic soda lye (5.5 ml) in a 250 ml flask. To it were charged 6-fluoro-3-(4-piperidinyl)-1,2-benzisoxazole (19.2 g) and sodium carbonate (34.6 g). The reaction mixture was heated to 85–90° C. for 4 hours under stirring, cooled to room temperature and filtered. The cake was purified by crystallisation from DMF.

The product was characterised by NMR spectroscopic studies as follows:

$^1$H NMR (60 MHz, CDCl$_3$): ∂ 7.5–7.9 (m, 1H); δ 6.8–7.45 (m, 2H); δ 3.8–4 (m, 2H) δ 2.45–3.5 (m, 11H); δ 2.35 (s, 3H); δ 1.65–2.25 (m, 8H).

Yield=30.0 g (72%).

Purity=99% (when analysed by HPLC).

What is claimed is:

1. A process for the preparation of a 3-substituted ethyl-6,7,8,9-tetrahydro-2-methyl-4H-pyrido[1,2-a]pyrimidin-4-one of formula IIB:

Formula IIB

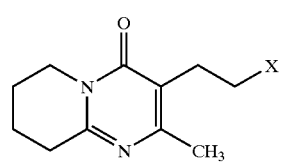

wherein X represents one of halogen, acyloxy and sulfonyloxy, comprising a hydrogenation of a substituted ethyl-2-methyl-4H-pyrido[1,2-a]pyrimidin-4-one of formula VB:

Formula VB

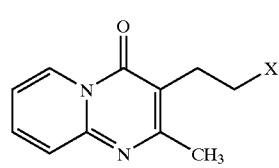

wherein X is as defined above, in an aqueous inorganic acid medium at a pressure of from atmospheric to 60 psi and at a temperature of from 0° to 100° C. in the presence of a metal catalyst, followed by an isolation of a resulting product.

2. The process of claim 1, wherein X represents tosyloxy.

3. The process of claim 1, wherein X represents mesyloxy.

4. The process of claim 1, wherein X represents Cl.

5. The process of claim 1, wherein the pressure is 25 psi.

6. The process of claim 1, wherein the inorganic acid comprises hydrochloric acid.

7. The process of claim 1, wherein the temperature is from 25° to 40° C.

8. The process of claim 1, wherein the metal catalyst comprises palladium supported on activated carbon.

9. The process of claim 1, wherein X represents one of Cl, tosyloxy and mesyloxy, the inorganic acid comprises hydrochloric acid, the pressure is 25 psi, the temperature is from 25° to 40° C., and the metal catalyst comprises palladium supported on activated carbon.

10. The process of claim 9, wherein X represents Cl.

11. A process for the preparation of 3-[2-[4-(6-fluoro-1,2-benzisoxazol-3-yl)-1-piperidinyl]ethyl]-6,7,8,9-tetrahydro-methyl-4H-pyrido[1,2-a]pyrimidin-4-one of formula I:

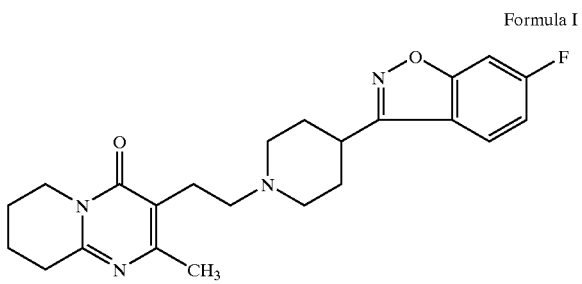

Formula I comprising a condensation of a 3-substituted ethyl-6,7,8,9-tetrahydro-2-methyl-4H-pyrido[1,2-a]pyrimidin-4-one of formula IIB:

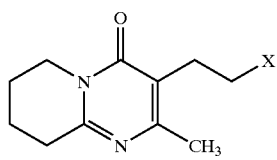

Formula IIB wherein X represents one of halogen, acyloxy and sulfonyloxy, with 6-fluoro-3-(4-piperidinyl)-1,2-benzisoxazole of formula IV:

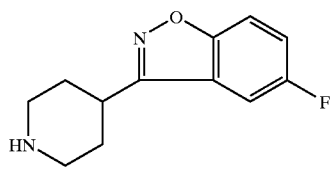

Formula IV in water and in the presence of an inorganic base at a temperature of from 25° to 100° C., followed by an isolation of a resulting product.

12. The process of claim 11, wherein X represents Cl.

13. The process of claim 11, wherein X represents one of tosyloxy and mesyloxy.

14. The process of claim 11, wherein the inorganic base comprises sodium carbonate.

15. The process of claim 11, wherein the temperature is from 60° to 90° C.

16. The process of claim 11, wherein the isolation comprises a purification, and the purification comprises a crystallization of the product from DMF.

17. The process of claim 11, wherein X is one of Cl, tosyloxy and mesyloxy, the inorganic base comprises sodium carbonate, and the temperature is from 60° to 90° C.

18. The process of claim 17, wherein X represents Cl.

19. The process of claim 18, wherein the temperature is from 85° to 90° C.

20. The process of claim 19, wherein the isolation comprises a purification, and the purification comprises a crystallization of the product from DMF.

* * * * *

UNITED STATES PATENT AND TRADEMARK OFFICE
CERTIFICATE OF CORRECTION

PATENT NO.    : 6,897,308 B1
DATED         : May 24, 2005
INVENTOR(S)   : R. Venkatasubramanian et al.

It is certified that error appears in the above-identified patent and that said Letters Patent is hereby corrected as shown below:

Title page,
Item [73], Assignee, "RGP" should be -- RPG --.

Column 8,
Line 24, "substituted" should be -- 3-substituted --.

Signed and Sealed this

Twenty-third Day of August, 2005

JON W. DUDAS
*Director of the United States Patent and Trademark Office*